(12) United States Patent
Bertolino et al.

(10) Patent No.: US 7,399,311 B2
(45) Date of Patent: Jul. 15, 2008

(54) MEDICAL DEVICES

(75) Inventors: William Bertolino, Framingham, MA (US); Andrew J. Campbell, Reading, MA (US); Steven Walak, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 481 days.

(21) Appl. No.: 10/212,508

(22) Filed: Aug. 5, 2002

(65) Prior Publication Data

US 2004/0024441 A1 Feb. 5, 2004

(51) Int. Cl.
*A61F 2/06* (2006.01)

(52) U.S. Cl. .................... 623/1.11; 623/1.23
(58) Field of Classification Search ............ 623/1.11, 623/1.23; 606/108, 194
See application file for complete search history.

(56) References Cited

U.S. PATENT DOCUMENTS

| | | | |
|---|---|---|---|
| 4,641,654 A * | 2/1987 | Samson et al. ............ 606/192 |
| 4,733,665 A | 3/1988 | Palmaz |
| 4,950,227 A | 8/1990 | Savin et al. |
| 4,960,227 A | 10/1990 | Coleman |
| 5,035,694 A | 7/1991 | Kasprzyk et al. |
| 5,114,423 A | 5/1992 | Kasprzyk et al. |
| 5,122,136 A | 6/1992 | Guglielmi et al. |
| 5,219,355 A * | 6/1993 | Parodi et al. ............ 606/191 |
| 5,234,457 A | 8/1993 | Andersen |
| 5,443,495 A | 8/1995 | Buscemi et al. |
| 5,545,135 A | 8/1996 | Iacob et al. |
| 5,643,278 A | 7/1997 | Wijay |
| 5,674,242 A | 10/1997 | Phan et al. |
| 5,697,882 A | 12/1997 | Eggers et al. |
| 5,725,570 A | 3/1998 | Heath |
| 5,752,935 A | 5/1998 | Robinson et al. |
| 5,795,318 A | 8/1998 | Wang et al. |
| 5,855,565 A * | 1/1999 | Bar-Cohen et al. ......... 604/104 |
| 5,925,075 A * | 7/1999 | Myers et al. ............. 623/1.13 |
| 6,036,697 A | 3/2000 | DiCaprio |
| 6,066,156 A | 5/2000 | Yan |
| 6,187,013 B1 * | 2/2001 | Stoltze et al. ............ 606/108 |
| 6,193,738 B1 | 2/2001 | Tomaschko et al. |
| 6,221,097 B1 | 4/2001 | Wang et al. |
| 6,224,592 B1 | 5/2001 | Eggers et al. |
| 6,312,461 B1 | 11/2001 | Unsworth et al. |
| 6,635,078 B1 * | 10/2003 | Zhong et al. ............. 623/1.11 |
| 2001/0003800 A1 | 6/2001 | Crowley |
| 2002/0116050 A1 * | 8/2002 | Kocur ................... 623/1.15 |

FOREIGN PATENT DOCUMENTS

WO  WO 02/24115  3/2002

OTHER PUBLICATIONS

Sheng-Ping Zhong, U.S. Appl. No. 09/895,415, "Coating a Medical Appliance with a Bubble Jet Printing Head", filed Jul. 2, 2001.
Brent C. Gerberding, U.S. Appl. No. 10/067,722, "Medical Devices", filed Feb. 4, 2002.

* cited by examiner

*Primary Examiner*—Bruce Snow
(74) *Attorney, Agent, or Firm*—Fish & Richardson P.C.

(57) ABSTRACT

A medical device system includes a catheter, an expandable prosthesis over the catheter, and a holding material between the catheter and the prosthesis. The holding material initially holds the prosthesis over the catheter.

25 Claims, 6 Drawing Sheets

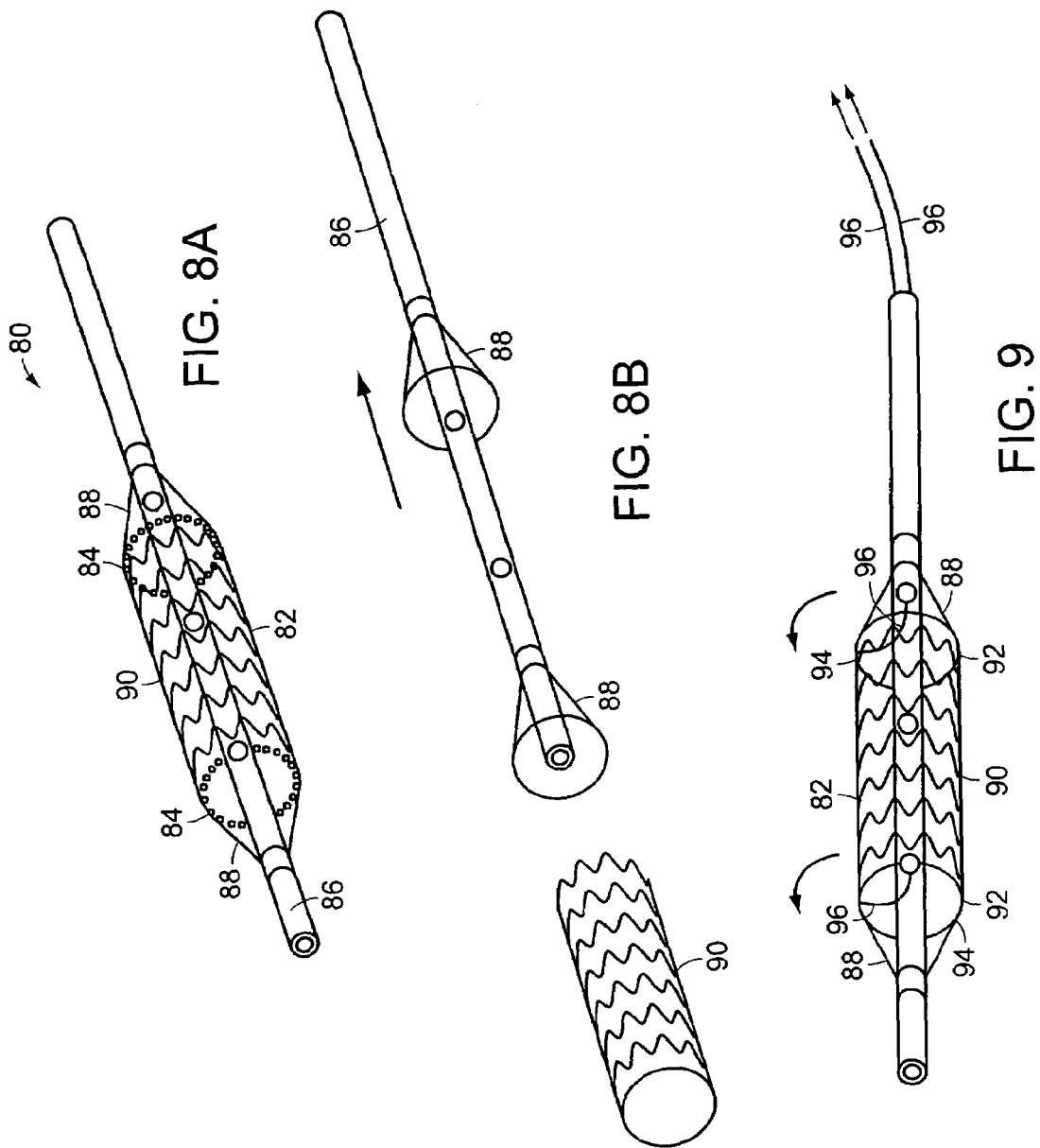

MEDICAL DEVICES

TECHNICAL FIELD

This invention relates to medical devices, such as endoprostheses, including methods of making and using them.

BACKGROUND

Medical endoprostheses such as stents can be placed within the body to perform a function such as maintaining open a body lumen, for example, a passageway occluded by a tumor or a blood vessel restricted by plaque. Other endoprostheses such as stent-grafts, or covered stents, can be used to substitute for or reinforce a lumen, such as the aorta or other blood vessels that have been weakened, e.g., by an aneurysm.

Endoprostheses can be delivered inside the body by a catheter that supports an endoprosthesis in a compacted or reduced-size form as the endoprosthesis is transported to a desired site. The size is particularly small when a percutaneous insertion technique is employed. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries the endoprosthesis. The balloon can be inflated so as to deform and fix the expanded endoprosthesis at a predetermined position in contact with the lumen wall. The balloon can then be deflated, and the catheter removed.

Balloon expandable endoprostheses can provide relatively good stiffness and relatively accurate placement. The force provided by the balloon also provides the endoprostheses with good vessel expansion and secure fixation. However, balloon expandable endoprostheses can have relatively low crush resistance, relatively low flexibility, and, in some cases, uncertain attachment to the expansion mechanism, e.g., the balloon.

In another delivery technique, the endoprosthesis is formed of an elastic material that can be reversibly compacted and expanded. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

Self-expandable endoprostheses can provide good flexibility and a persistent radial expansion force, which can provide good crush resistance. However, self-expandable prostheses can have relatively inconsistent or poor placement accuracy. In some cases, a separate balloon dilation procedure is necessary to ensure proper expansion and contact. Furthermore, the restraining device can increase the cross sectional profile of the endoprosthesis, which can limit the number of implantation sites where the endoprosthesis can be used.

SUMMARY

This invention relates to medical devices, such as endoprostheses, including methods of making and using them.

In one aspect, the invention features medical device systems having a prosthesis, such as a stent or a stent-graft, attached directly to a catheter, for example, by a holding material such as an adhesive. The attachment between the prosthesis and the catheter can be selectably modified to effect expansion of the prosthesis and separation of the prosthesis from the catheter. All or only a portion of the prosthesis can be controllably separated from the catheter.

In another aspect, the invention features a medical device system including a catheter, an expandable prosthesis over the catheter, and a holding material between the catheter and the prosthesis. The holding material initially holds the prosthesis over the catheter.

Embodiments may include one or more of following features. The prosthesis is not completely expanded. The catheter includes a lumen in fluid communication with the holding material. The system includes a heatable wire extending between the catheter and the prosthesis. The exterior surface of the prosthesis is substantially exposed. The prosthesis is capable of exerting a radial, expansion force. The prosthesis is self-expandable. The prosthesis is separable from the catheter. The prosthesis is a stent or a stent-graft. The holding material is an adhesive. The system includes two axially movable sleeves initially holding end portions of the prosthesis to the catheter.

The system may be free of a constraining device extending over substantially a whole length of the prosthesis, and/or free of an inflatable balloon between the catheter and the prosthesis.

The prosthesis can include a first portion separable from the catheter, and a second portion inseparable from the catheter. The prosthesis can include a detachable portion between the first and second portions. The prosthesis can include a structurally weakened portion between the first and second portions. The prosthesis can include a degradable portion between the first and second portions. The prosthesis may include a wire having two portions with different electrical resistance.

In another aspect, the invention features a method of using a medical device system. The method includes positioning the system at a predetermined site, and releasing the prosthesis from the catheter. The system includes a catheter, an expandable prosthesis over the catheter, and a holding material between the catheter and the prosthesis. The holding material initially holds the prosthesis over the catheter.

Embodiments may include one or more of following features. The method includes contacting the holding material with a fluid that releases the hold between the catheter and the prosthesis. The fluid is introduced through a lumen in fluid communication with the holding material. The method includes applying monopolar radiofrequency and/or bipolar radiofrequency energy. The prosthesis is separated from the catheter adjacent to an aneurysm.

The method may include exposing the holding material to a condition that modifies the hold between the catheter and the prosthesis. The condition can be a change in temperature, a change in pH, and a change in pressure.

Embodiments may have one or more of the following advantages. The medical device systems can have a relatively small profile compared to, for example, systems having an outer prosthesis restraining device or systems having an inflatable balloon between the prosthesis and the catheter. As a result, the systems can require relatively low insertion and withdrawal forces. The systems can be used in relatively narrow and/or tortuous sites.

The systems can include benefits of self-expandable and balloon expandable prostheses. For example, the systems can include a self-expandable prosthesis with high resiliency, good flexibility, and crush resistance. The self-expandable prosthesis can provide a persistent radial force. The systems can accurately deploy a prosthesis in a single step. For example, unwanted movement of the prosthesis during deployment, such as, for example, slippage beyond an intended site, can be reduced. The systems can require relatively few parts, which reduces cost and complexity of fabrication. In some embodiments, the systems are integrated, and can be used to dilate the intended site and to deliver a prosthesis. In some embodiments, no protective outer sheath over the prosthesis is needed. The prosthesis is securely attached to the catheter, and in certain embodiments, the prosthesis can be reconstrained after partial expansion.

Other features and advantages of the invention will be apparent from the description of the preferred embodiments thereof and from the claims.

DESCRIPTION OF DRAWINGS

FIGS. 8A and 8B are schematic diagrams of an embodiment of a medical device system, including a method of using the system.

FIG. 9 is a schematic view of an embodiment of a medical device system.

DETAILED DESCRIPTION OF THE PREFERRED EMBODIMENTS

Figure 1A:
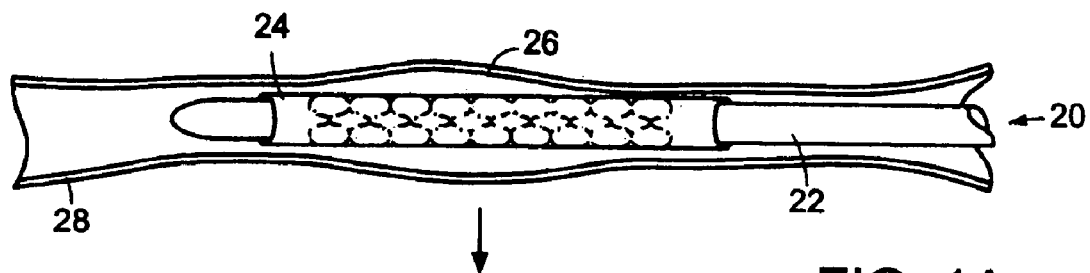
FIGS. 1A, 1B, 1C, and 1D are schematic diagrams of an embodiment of a medical device system, including a method of using the system.

FIG. 1A shows a medical device system 20 including a catheter 22 and an expandable prosthesis 24 attached to the catheter. Prosthesis 24 is attached, at least initially, in a fully or partially compacted state. As shown, system 20 does not include an inflatable balloon between catheter 22 and prosthesis 24, or a restraining device, such as a sheath, over the prosthesis. As a result, system 20 has a relatively small profile and requires relatively low insertion and withdrawal forces, such that the system can be used in relatively narrow and/or tortuous sites.

Prosthesis 24 can be a conventional stent or a conventional stent-graft. For example, the stent can be made of Nitinol. The stent-graft can be, for example, a stent made of Nitinol or Elgiloy™ stainless steel, in a biocompatible, non-porous or semi-porous polymer matrix made of polytetrafluoroethylene (PTFE), expanded PTFE, polyethylene, polyethyleneterephtalate (PET), polybutyleneterephthalate (PBT), urethane, or polypropylene. Prosthesis 24 can be balloon expandable, self-expandable, or a combination of both. Examples of prosthesis 24 are described in U.S. Pat. Nos. 4,733,665, 4,960, 227, 5,234,457, and 5,725,570, all hereby incorporated by reference. Prosthesis 24 can also include a releasable drug, such as described in U.S. Pat. No. 5,674,242, and commonly-assigned U.S. Ser. No. 09/895,415, filed Jul. 2, 2001, all hereby incorporated by reference. Prosthesis 24 can include side ports adapted for perfusion, as described in U.S. Pat. No. 5,545,135, hereby incorporated by reference.

Catheter 22, as described in embodiments below, is generally adapted such that prosthesis 24 can be attached to the catheter and expanded. All or a portion of the prosthesis can be separated from the catheter. For example, the inner wall of prosthesis 24 can be directly attached to the outer surface of catheter 22, and all or part of the prosthesis can be detached from the catheter and secured to a deployment site.

Figure 1B:
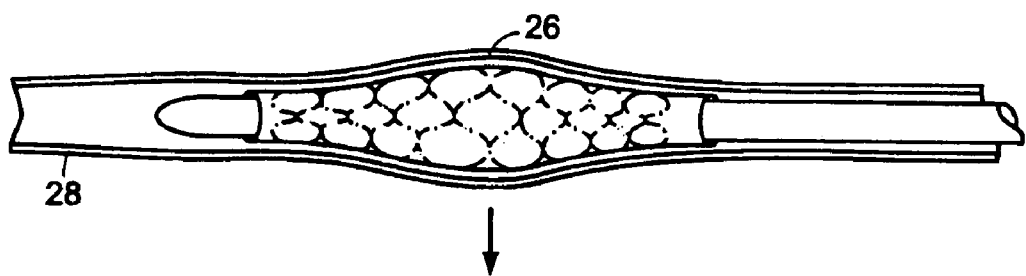
Figure 1C:
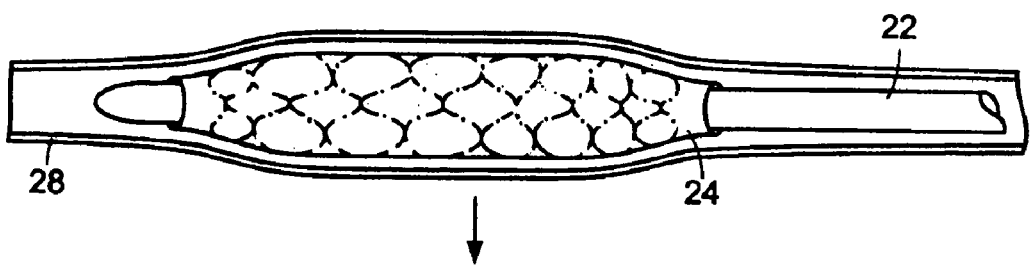
Figure 1D:
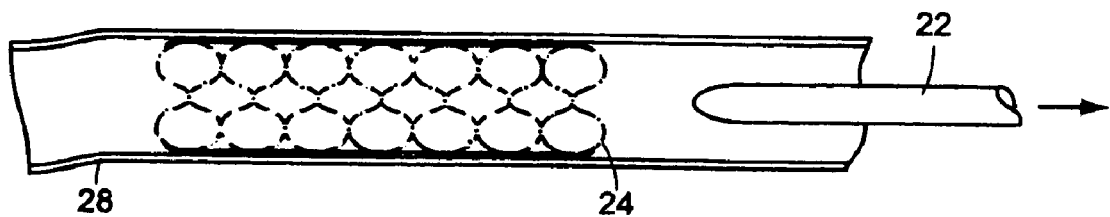

Referring to FIGS. 1A-1D, a method of using medical system 20 generally includes positioning prosthesis 24 (attached to catheter 22) at a predetermined deployment site, expanding the prosthesis, and separating the prosthesis from the catheter. In some embodiments, a compressed prosthesis 24, e.g., a self-expandable stent-graft, is positioned adjacent to an aneurysm 26 in a vessel 28 by conventional methods, e.g., by passing an emplaced guidewire through a guidewire lumen (not shown) of the catheter (FIG. 1A). Prosthesis 24 is then expanded by releasing the attachment between the prosthesis and catheter 22 (FIGS. 1B and 1C). When prosthesis 24 is expanded to the desired size, e.g., until it contacts vessel 28 or is secured to the vessel, the prosthesis is separated from catheter 22, and the catheter is withdrawn (FIG. 1D).

Figure 2:
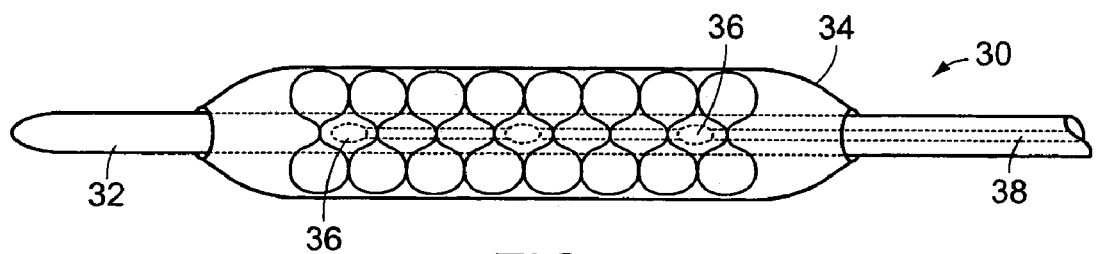
FIG. 2 is a schematic view of an embodiment of a medical device system.

Referring to FIG. 2, in some embodiments a medical device system 30 includes a catheter 32 and an expandable prosthesis 34, here, a self-expandable stent-graft, attached near the distal end of the catheter, by a holding material between the prosthesis and the catheter. Catheter 32 includes a guidewire lumen (not shown) for delivering prosthesis 34 to a desired site, and a plurality of ports 36. Ports 36 are in fluid communication with the interior of prosthesis 34 and a lumen 38, which extends within catheter 32 to the proximal end of the catheter. In some embodiments, system 30 can have one port 36, e.g., one that extends substantially the full length of prosthesis 34. Initially, prosthesis 34 can be fully or partially compressed over catheter 32, e.g., by applying holding material between the catheter and the prosthesis and applying suction through ports 36 via lumen 38.

The holding material, for example, an adhesive, can be any material that can attach the compressed prosthesis to the catheter for delivery, and that can be subsequently modified to release the attachment, thereby allowing the prosthesis to expand. For example, the holding material can dissolve, degrade, react, or fail to function as an effective holding material upon exposure to a stimulus. In embodiments wherein prosthesis 34 is a self-expandable stent-graft, modifying the holding material can allow the stent-graft to expand, e.g., by its own expansion force.

Examples of stimuli include a change in temperature, a change in pH, a change in pressure, an exposure to certain chemicals, i.e., a chemical reaction, and an exposure to energy such as optical or electrical energy. Examples of suitable adhesives include polyvinyl alcohol (which dissolves in a solution having a selected pH, e.g., about >7.4), and polyvinyl acetates, or vinyl or collagen based glues or gelatins (which fails at a selected burst pressure, e.g., greater than about 255 psi). Other degradable materials are described in Buscemi et al., U.S. Pat. No. 5,443,495, hereby incorporated by reference. The holding material, the stimulus, and the product of the reaction between the holding material and the stimulus are preferably safe for medical uses.

During use, prosthesis 34 is introduced to the desired site, e.g., via a guidewire, with the prosthesis compressed and attached to catheter 32 by a selected holding material (e.g., FIG. 1A). When prosthesis 34 is appropriately positioned, a stimulus is introduced to the prosthesis to modify the holding material so that the prosthesis can expand (e.g., FIGS. 1B and 1C). If the holding material is heat sensitive, e.g., degrades at a certain temperature, the holding material can be degraded by introducing a fluid heated to the degradation temperature through ports 36 via the proximal end of expansion lumen 38. If the holding material loses its effectiveness at a certain pH, a fluid of appropriate pH can be introduced. If the holding material loses its effectiveness when it reacts with a second material, the second material can be introduced through the expansion lumen. If the holding material fails under pressure, pressurized gas or fluid can be introduced through the expansion lumen. If the holding material fails when exposed to energy, e.g., ultraviolet light, an optic fiber can be configured through expansion lumen 38 to emit the appropriate energy through ports 36. In some embodiments, the holding material may degrade upon exposure to a bodily environment, e.g., blood.

As the stimulus modifies the holding material, e.g., degrades or dissolves the adhesive, prosthesis 34 expands, e.g., under its self-expansion force, away from catheter 32 (e.g., FIGS. 1B and 1C). In some embodiments, the stimulus, such as a gas or a liquid, can also provide internal pressure to expand or inflate the prosthesis, e.g., as with inflatable balloons. These embodiments take advantage of the ability of stent-grafts to hold pressure. Introduction of the stimulus can eventually completely modify the holding material such that the prosthesis can separate from the catheter (e.g., FIG. 1D). That is, the stimulus can also remove holding material that is securing the ends of the prosthesis to the catheter.

Other methods of modifying the holding material can be used.

Figure 6:
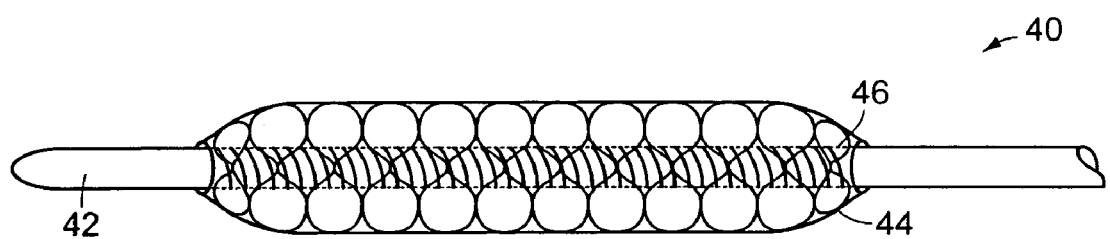
FIG. 6 is a schematic view of an embodiment of a medical device system.

Referring to FIG. 6, in some embodiments, the holding material can be modified by electrical energy, e.g., heat. System 40 includes a catheter 42, a self-expandable prosthesis 44 attached to the catheter by a holding material, and an electrical wire 46 that is wrapped around the catheter and extends to a current source via a catheter lumen (not shown). In some embodiments, catheter 42 can be formed having a portion of its length with a reduced outer diameter, i.e., recessed, where prosthesis 44 is attached the catheter so that the windings of wire 46 do not increase the profile of system 40. Wire 46 can be replaced by or be used with any electrically conductive portion, e.g., a metal tube.

In use, the holding material is modified, e.g., degraded, by passing a current through wire 46. The current can heat wire 46, and the heat can degrade, e.g., melt or erode, the holding material. When the holding material degrades sufficiently, self-expanding prosthesis 44 separates from catheter 42, e.g., to engage with a vessel wall, and the catheter can be withdrawn. The catheter can be configured with multiple, independently-controllable portions, i.e., wire coils, along its axial length to provide controlled modification, expansion and separation. For example, the catheter can include a middle wire coil independently controllable from two end wire coils adjacent to the middle coil. During use, the middle coil can be heated first to effect expansion of the prosthesis, followed by heating the end wire coils to complete expansion and/or separation of the prosthesis.

Figure 7:
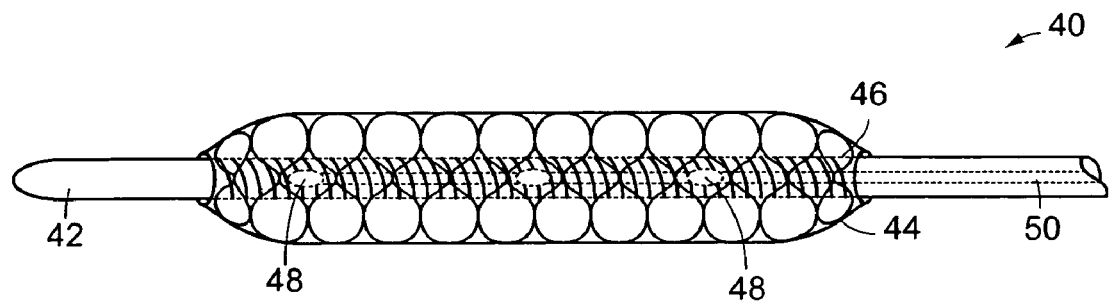
FIG. 7 is a schematic view of an embodiment of a medical device system.

Referring to FIG. 7, in some embodiments, system 40 can include ports 48, as described above. During use, the holding material can be modified by passing a current through wire 46 and/or by passing a stimulus through a lumen 50. System 40 with ports 48 can be used to deliver an expansion fluid to expand prosthesis 44, e.g., a non-self-expandable prosthesis. For example, the holding material can be modified by passing a current through wire 46; prosthesis 44 can be expanded by an expansion fluid introduced through ports 48; the fluid can be removed by applying suction through the ports; and the prosthesis can be separated by passing a current through the wire.

In some embodiments, the holding material can be modified electrically by configuring the catheter as an active electrode of a monopolar radiofrequency (RF) system, with another electrode, e.g., a return pad, external of a patient. For example, a catheter can include a conductive portion, e.g., a wire coil or a metallic tube, between the catheter and the prosthesis that acts as an electrode. During use, RF current flows from an output connection on a power unit to the active electrode, through the patient, and then returns to the power unit via the return pad. Alternatively or in addition, a bipolar RF system can be used in which two distinct portions of the catheter serve as the electrodes. For example, one electrode can be formed next to the holding material and under the prosthesis, and the other electrode can be formed on the catheter distally or proximally of the prosthesis. The radiofrequency can be constrained to about 460,000 Hz, e.g., as in liver ablation devices. Medical uses of monopolar and bipolar RF systems are described, for example, in U.S. Pat. Nos. 5,681,232, 5,697,882, and 6,224,592, all hereby incorporated by reference.

The catheter can be configured with multiple, independently-controllable portions, i.e., active electrodes, along its axial length to provide controlled modification, expansion and separation.

Figure 13:
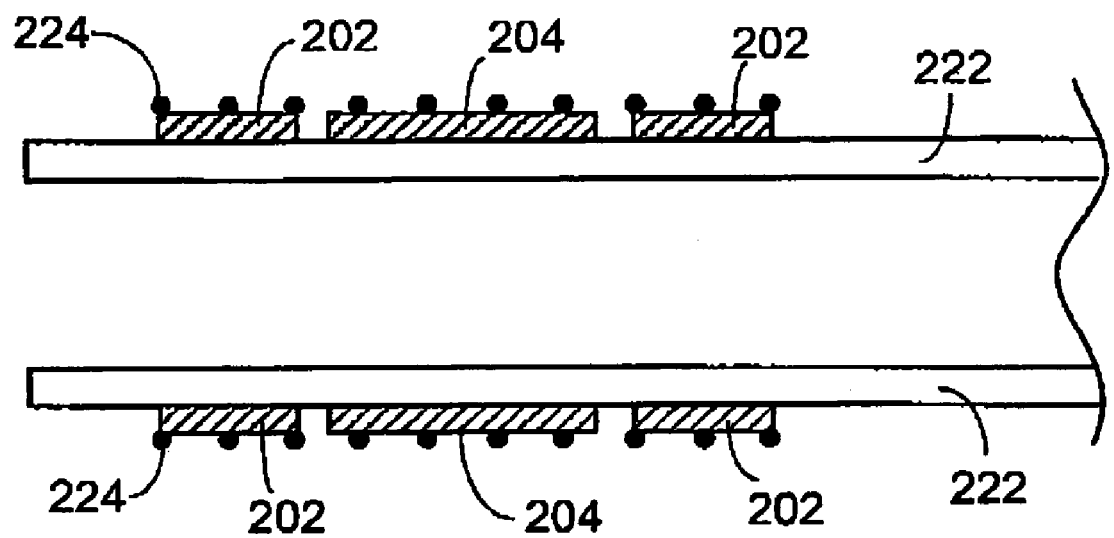
FIG. 13 is a cross-sectional view of an embodiment of a medical device system.

In some embodiments, more than one type of holding material can be used to provide more control in deploying the prosthesis. As shown in FIG. 13, for example, a first holding material 202 can be used to secure the ends of a prosthesis 224 to a catheter 222, and a second holding material 204 can be used to secure the body of prosthesis 224 to catheter 222. A first stimulus can be introduced to react with second holding material 204 so that prosthesis 224 can expand. The first stimulus can then be removed, e.g., by suction. A second stimulus can then be introduced to react with first holding material 202 so that prosthesis 224 can be separated from catheter 222.

In some embodiments, the holding material can be profiled, e.g., non-uniform, between the prosthesis and the catheter. For example, more holding material can be used near the ends of the prosthesis than near the body of the prosthesis to provide relatively slower prosthesis separation than prosthesis expansion.

Figure 12:
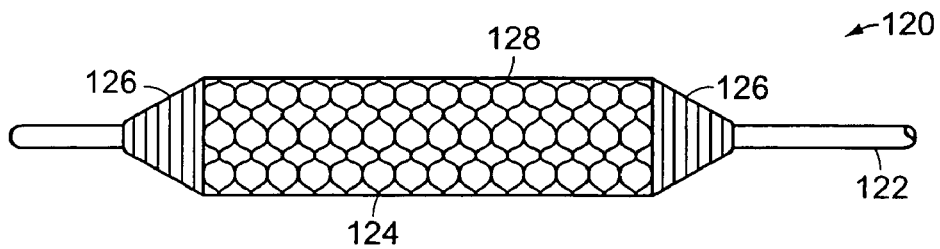
FIG. 12 is a schematic view of an embodiment of a medical device system.

Referring to FIG. 12, in embodiments, the prosthesis can be modified to provide selected expansion and separation. System 120 includes a prosthesis 124, here, a stent-graft, made of two or more materials. Prosthesis 124 can be initially attached to a catheter 122 with a holding material as described above. Prosthesis 124 includes tapered regions 126 made of a shape memory metal, such as Nitinol, and dilatation portion 128 made of, for example, stainless steel. The composition of the shape memory material of tapered regions 126 can be controlled to activate phase transformation and shape transition at a predetermined temperature.

In use, prosthesis 124 is delivered to a desired site attached to catheter 122 by a holding material. Then, a stimulus is introduced to modify the holding material, as described above. In some embodiments, the stimulus is heating to a temperature above the predetermined phase transition temperature of the shape memory material. When exposed to temperatures above its transition temperature, the shape memory material can undergo phase transformation and shape change. As a result, tapered regions 126 can spring radially outward, separating prosthesis 124 from catheter 122, and prop open dilatation portion 128, e.g., like a spring-loaded tent. In certain embodiments, modification of the holding material and separation of prosthesis 124 can be performed in two stages. For example, a first stimulus can be introduced to modify the holding material and then removed from between the prosthesis and the catheter, e.g., via suction through a catheter lumen. Subsequently, a second stimulus can be introduced to induce a temperature change in the shape memory material to effect prosthesis separation and expansion.

In certain embodiments, the catheter can include multiple ports in fluid communication with multiple separate catheter lumens. This arrangement can provide control of prosthesis expansion and separation. For example, a stimulus can be introduced along the length of the catheter in a predetermined sequence.

Other Embodiments

Numerous embodiments and combinations can be used for attaching prosthesis 24 to catheter 22, expanding the prosthesis, and separating the prosthesis from the catheter.

Generally, methods of attaching prosthesis 24 to catheter 22 are selected such that the prosthesis can be delivered to the predetermined site in a relatively compact form. For example, prosthesis 24 can be attached directly to catheter 22 without having a sheath surrounding the prosthesis such that the entire exterior surface of the prosthesis is exposed. The attachment should be controllably removable or releasable so that prosthesis 24 can be expanded and separated from catheter 22. Examples of attachment methods include chemical methods as described above, mechanical methods, magnetic methods, or combinations of these methods.

Expanding the prosthesis generally removes or releases the attachment between the prosthesis and the catheter so that the prosthesis can be deployed. Methods of expanding the prosthesis are selected to provide accurate and precise deployment of the prosthesis, e.g., without the prosthesis shifting undesirably during deployment. Methods of expanding the prosthesis can be chemical, mechanical, electrical, magnetic, or combinations of these methods.

Separating the prosthesis from the catheter allows the prosthesis to function, e.g., by engaging a vessel wall, and allows the catheter to be withdrawn from the deployment site. All or only a portion of the prosthesis can be separated from the catheter.

Some methods of attaching the prosthesis to the catheter are described below.

Figure 3:
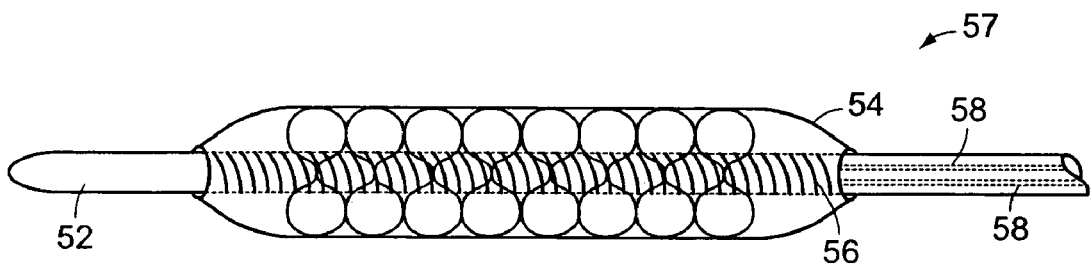
FIG. 3 is a schematic view of an embodiment of a medical device system.

Alternatively or in addition to using a holding material, a prosthesis can be attached to a catheter magnetically. Referring to FIG. 3, in embodiments, medical device system 51 includes a catheter 52 and a prosthesis 54, e.g., a self-expandable stent, attached to the catheter. Prosthesis 54 is formed of a material, e.g., iron, cobalt, and their alloys, that can be attracted to a magnet. Catheter 52 includes a wire 56 coiled about the catheter between the catheter and prosthesis 54, e.g., to form a solenoid. Wire 56 extends through lumens 58 of catheter 52 to the proximal end of system 51, where the ends of the wire are connected to a current source (not shown). By flowing a current through wire 56, the coil of wire can serve as an electromagnet that attracts prosthesis 54 radially inwardly, thereby causing the prosthesis to be compacted about and attached to catheter 52.

Prosthesis 54 can be expanded by stopping the flow of current through wire 56, thereby releasing the magnetic attraction to the wire and allowing the prosthesis to self-expand. As described above, a stimulus can be introduced to modify the holding material, if necessary. In embodiments wherein the prosthesis is attached to the catheter only by magnetic methods, the prosthesis can be separated from the catheter by stopping the flow of current through the wire of the electromagnet.

In some embodiments, the catheter includes multiple independently operable electromagnets, e.g., to provide more control of prosthesis expansion and separation. For example, the ends of the prosthesis can be attached to the catheter by a first set of electromagnet(s), and the middle portion or body of the prosthesis can be attached by a second set of electromagnet(s). During use, the prosthesis can be expanded by stopping the flow of current through the second set of electromagnet(s). When the prosthesis is expanded to desired level, the first set of electromagnet(s) can be deactivated to further expand the prosthesis and/or to separate the prosthesis from the catheter. The electromagnets can be continuous or non-continuous along the axial length of the catheter.

Figure 4:
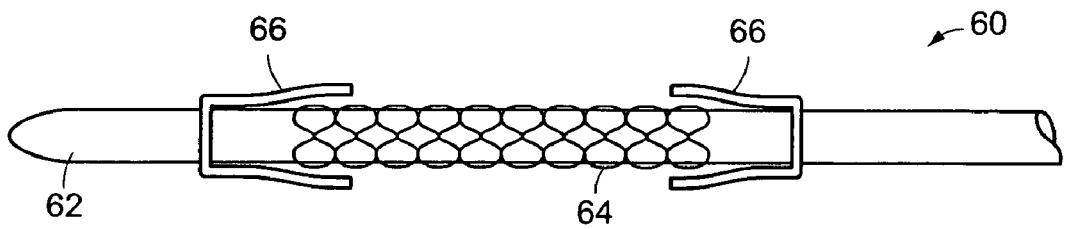
FIG. 4 is a schematic view of an embodiment of a medical device system.

Alternatively, or in addition, a prosthesis can be attached to a catheter mechanically. Referring to FIG. 4, system 60 includes a catheter 62 and a prosthesis 64 attached to the catheter by a pair of resilient tubular members 66 at the ends of the prosthesis. Tubular members 66 provide a temporarily prosthesis securing mechanism and can roll back onto themselves as prosthesis 64 expand. An example of tubular members 66 is described in Savin et al., U.S. Pat. No. 4,950,227, and Wang et al., U.S. Pat. No. 6,221,097, hereby incorporated by reference.

Figure 5:
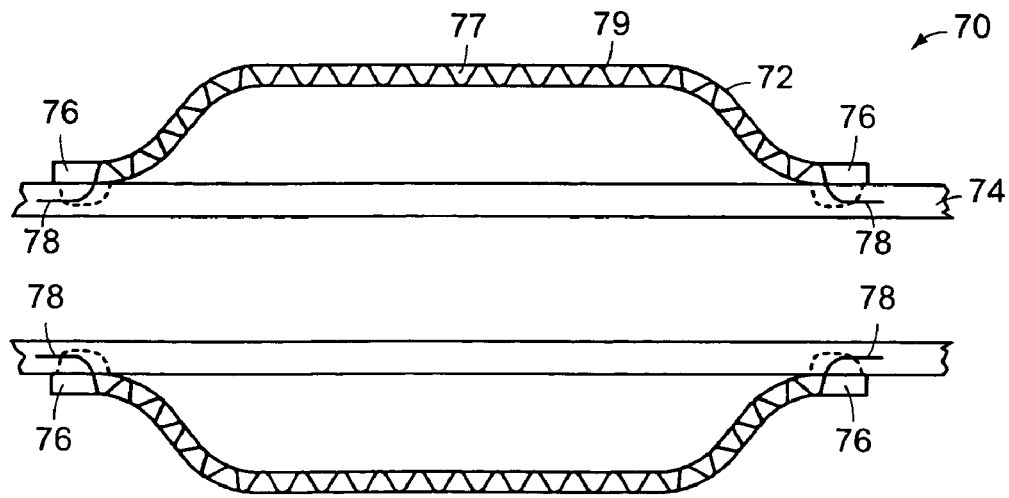
FIG. 5 is a schematic view of an embodiment of a medical device system.

FIG. 5 shows another system having a prosthesis mechanically attached to a catheter. System 70 includes a prosthesis 72, here, a stent-graft, having portions 76 of graft 77 attached to the exterior surface of catheter 74, for example, by a holding material such as an adhesive. Prosthesis 72 also includes portions 78 of stent 79 that extend into a wall of catheter 74. Stent portions 78 are secured to catheter 74, for example, by spot welding. Portions 78 provide another method of securing prosthesis 72 to catheter 74. Remaining portions of prosthesis 72 can be attached to catheter 74 by a holding material, as described above. The bonds between graft portions 76 and catheter 74, and between stent portions 78 and the catheter, are formed to fail under predetermined stimuli, e.g., exposure to a chemical or certain pressure, so that prosthesis 72 can be separated from the catheter during use.

Figure 11:
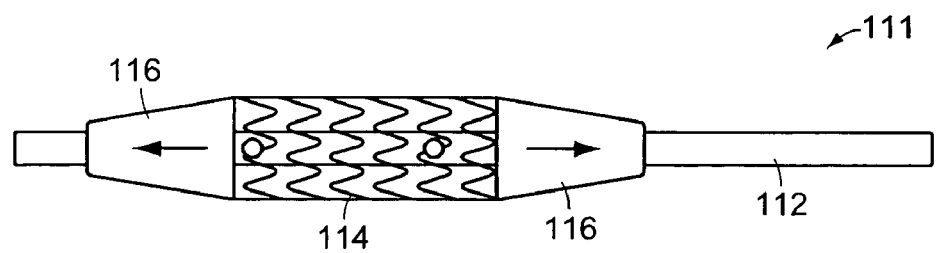
FIG. 11 is a schematic view of an embodiment of a medical device system.

FIG. 11 shows another system having a prosthesis mechanically attached to a catheter. System 111 includes a catheter 112 and a prosthesis 114 attached to the catheter by two end caps 116. End caps 116 provide a temporarily prosthesis securing mechanism and can be displaced, e.g., by a mechanical screw drive, so that prosthesis 114 can expand and/or separate from catheter 112.

In some embodiments, a prosthesis is attached to a catheter by a combination of methods. For example, the prosthesis can be chemically and magnetically attached, or mechanically and magnetically attached.

While the prosthesis can be completely separated from the catheter as described above, in some embodiments, only a portion of the prosthesis is separated from the catheter. The portion of the prosthesis can be separated, for example, mechanically, electrically, or chemically. The prosthesis can be separated from the catheter in substantially one step or sequentially, e.g., a first end and then a second end.

Referring to FIG. 8A, system 80 includes a prosthesis 82 (here, a stent-graft) having separation zones 84, and a catheter 86. Prosthesis 82 can be attached to catheter 86 and expanded by any of the methods described herein. Zones 84 define areas that separate a portion of prosthesis 82 that can separate from catheter 86 and portions that remain attached to the catheter after deployment of the prosthesis. For example, separation zones 84 can be formed between tapered regions 88 and body portion 90 of prosthesis 82. In some embodiments, separation zones 84 are areas of prosthesis 82 that fail, e.g., ruptures or tears, under a predetermined condition, e.g., at a selected pressure. Examples of a separation zone are prosthesis cross sections that have reduced thickness, that have been pre-scored, thinned, or scribed, or that have reduced resistance to mechanical stress, i.e., weakened. Methods of making a separation zone is described in Tomaschko, et al. U.S. Pat. No. 6,193,738, and commonly-assigned U.S. Ser. No. 10/067,722, filed Feb. 4, 2002, all hereby incorporated by reference in its entirety.

During use, prosthesis 82 is expanded from catheter 86 as described herein. When the prosthesis is expanded to the desired level, body portion 90 is separated from catheter 86 by introducing the predetermined condition, e.g., increased pressure, to the prosthesis, which causes zones 82 to tear. After body portion 90 separates from catheter 86, the catheter with tapered regions 88 attached thereto is withdrawn (FIG. 8B). Tapered regions 88 can be formed of a relatively pliable material so that they do not displace prosthesis 82 when catheter 86 is withdrawn.

Referring to FIG. 9, in certain embodiments, body portion 90 can be separated by manually tearing separation zones 92. Separation zones 92 include removable, e.g., prescored, strips 94 that connect body portion 90 and tapered portions 88. Strips 94 are connected to rip cords 96 that extend through catheter lumens (not shown) to the proximal end of catheter 86. Separation zones 92 can be formed anywhere along the length of prosthesis 82.

In use, zones 92 operate similarly to a cellophane wrapper of a cigarette box or a chewing gum wrapper having a tear-away and removable seal. That is, after prosthesis 82 is expanded to the desired level, rip cords 96 are pulled proximally which causes strips 94 to tear away from prosthesis 82 and separates body portion 90 from catheter 86. Catheter 86 with tapered regions 88 attached thereto can then be withdrawn.

In some embodiments, a prosthesis can include different types of separation zones. For example, a prosthesis can include a distal separation zone that can be ruptured by pressure and a proximal separation zone that can be torn mechanically with a rip cord. In use, after the prosthesis is expanded, the distal end of the body portion can be separated from the catheter, e.g., by increasing the internal pressure. Subsequently, the proximal end can be separated by pulling on the rip cord.

Figure 10:
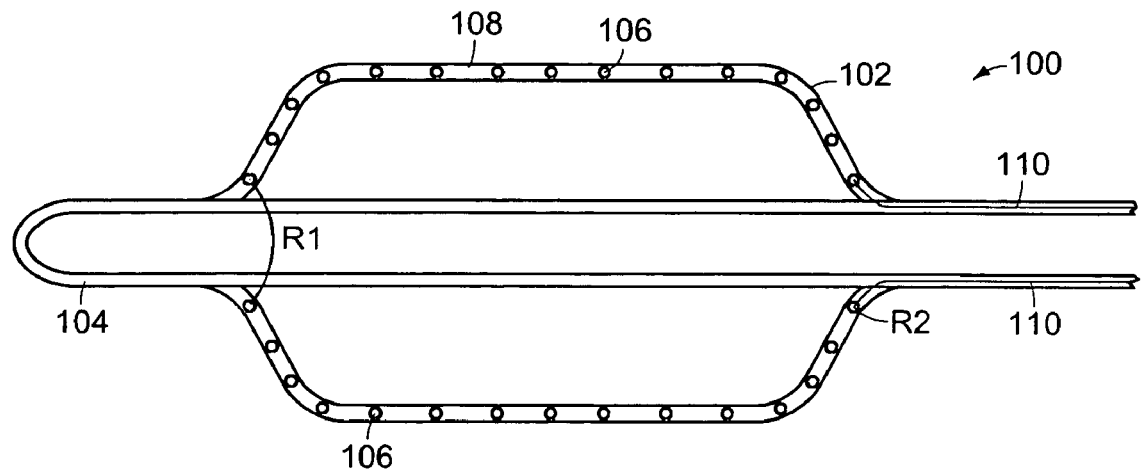
FIG. 10 is a schematic view of an embodiment of a medical device system.

In certain embodiments, all or a portion of a prosthesis can be separated from a catheter electrically. Referring to FIG. 10, system 100 includes a prosthesis 102 attached to a catheter 104. Prosthesis 102 can be attached to catheter 104 and expanded by appropriate methods described herein. Prosthesis 102, here, a stent-graft, includes a continuous, electrically conducting framework of wire 106 in a graft 108. System 100 further includes two wires 110 that, at the distal end, are connected to framework of wire 106 at the proximal end of prosthesis 102. At the proximal end, wires 110 are connected to a current source (not shown). Prosthesis 102 is fabricated such that, at its proximal end, the prosthesis has a portion of wire 106 that has a predetermined electrical resistance ($R_2$) greater than a predetermined electrical resistance ($R_1$) of a portion of wire 106 at the distal end of the prosthesis. Electrical resistances $R_1$ and $R_2$ are selected such that the corresponding portions of wire 106 will fail, e.g., melt or erode, at selected currents. The remaining portions, e.g., the middle body portion, of the prosthesis should remain intact.

In operation, after prosthesis 102 is expanded to the desired level, a current is passed through wire 110 from the current source. Since prosthesis 102 is formed of a continuous framework of wire 106, current can flow from the proximal end to the distal end of the prosthesis. At a first predetermined current, the distal portion of wire 106 having electrical resistance $R_1$ fails, thereby acting as a separation zone and allowing the distal portion of the prosthesis to separate from the catheter. Similarly, at a second predetermined current, the proximal portion of wire 106 having electrical resistance $R_2$ fails, thereby separating the prosthesis from the catheter. Portions of wire 106 having resistance $R_1$ and $R_2$ can be fabricated anywhere along the length of the prosthesis, including the area between the body portion and the tapered portions. Other methods of electrically severing a conductive wire is described in Guglielmi et al., U.S. Pat. No. 5,122,136, hereby incorporated by reference.

Still in other embodiments, all or a portion of a prosthesis can be separated from a catheter chemically. The prosthesis can include portions made of materials that alter, e.g., degrade, upon exposure to a stimulus. For example, the prosthesis can include tapered regions or separation zones made of materials that degrade upon exposure to another material, heat, optical energy, e.g., ultraviolet radiation, electrical energy, or vibrational energy. The stimulus can be delivered, for example, through ports of the catheter, as described above. In some embodiments, the portions can have the form tubular members 66 (FIG. 4) that externally compress the prosthesis.

Examples of degradable materials are described in Buscemi et al., U.S. Pat. No. 5,443,495, hereby incorporated by reference in its entirety. For example, degradable portions may include a polymer that has labile components adapted to cause a chain scission reaction or may include a polymer that is cleaved by a secondary, energy activated compound and which breaks down into components that are soluble and disperse. The polymers that may be used can be natural, synthetic or a modified natural polymer such as a conjugated protein. An example of a material is a linear polyester prepared from 2-hydroxy-1-[4-(2-hydroxyethoxy)phenyl]-2-methyl-1-propanone, dimethyl succinate and zinc stearate. Along with the linear polyester is mixed 4-methoxyphenol. A second polymer may be a linear polyester prepared from 2-hydroxy-1-[4-(2-hydroxyethoxy)phenyl]-2-methyl-1-propone, dimethyl fumarate, dimethylsebacate, and zinc stearate mixed with 4-hydroxyphenyloctyl ether.

In other embodiments, the medical systems described above can be used with a restraining device, such as, for example, an outer sheath that goes over the catheter and the prosthesis. In some embodiments, an inflatable balloon can be placed between the catheter and the prosthesis. The medical systems described above can include radiopaque markers to help the user position the prosthesis. For example, the wire of the stent or stent-graft can be radiopaque, e.g., includes gold or tantalum.

Other embodiments are within the claims.

The invention claimed is:

1. A medical device system, comprising:
   a catheter;
   an expandable prosthesis over the catheter; and
   first and second holding materials between the catheter and the prosthesis, the holding materials initially holding the prosthesis in a compacted state over the catheter, the first holding material being modifiable by a first stimulus, and the second holding material being modifiable by a second stimulus and not the first stimulus, wherein the system is free of an inflatable balloon between the catheter and the prosthesis, and free of a constraining device over the prosthesis when the prosthesis is held in the compacted state.

2. The system of claim 1, wherein the catheter comprises a lumen in fluid communication with one or more of the holding materials.

3. The system of claim 1, further comprising a heatable wire extending between the catheter and the prosthesis.

4. The system of claim 1, wherein the exterior surface of the prosthesis is substantially exposed.

5. The system of claim 1, wherein the prosthesis is capable of exerting a radial, expansion force.

6. The system of claim 1, wherein the prosthesis is self-expandable.

7. The system of claim 1, wherein the prosthesis is separable from the catheter.

8. The system of claim 1, wherein the prosthesis comprises a first portion separable from the catheter, and a second portion inseparable from the catheter.

9. The system of claim 8, wherein the prosthesis further comprises a detachable portion between the first and second portions.

10. The system of claim 8, wherein the prosthesis further comprises a structurally weakened portion between the first and second portions.

11. The system of claim 8, wherein the prosthesis further comprises a degradable portion between the first and second portions.

12. The system of claim 1, wherein the prosthesis comprises a wire having two portions with different electrical resistance.

13. The system of claim 1, further comprising two axially movable sleeves initially holding end portions of the prosthesis to the catheter.

14. The system of claim 1, wherein the prosthesis is a stent.

15. The system of claim 1, wherein the prosthesis is a stent-graft.

16. The system of claim 1, wherein the first and second holding materials are adhesives.

17. The system of claim 1, free of a constraining device extending over substantially a whole length of the prosthesis.

18. The system of claim 2, wherein the catheter defines a port that fluidly connects the lumen with one or more of the holding materials.

19. The system of claim 1, wherein the first holding material is modifiable by one or more stimuli selected from the group consisting of a change in temperature, a change in pH, a change in pressure, an exposure to one or more chemicals, and an exposure to energy.

20. The system of claim 19, wherein the second holding material is modifiable by one or more stimuli selected from the group consisting of a change in temperature, a change in pH, a change in pressure, an exposure to one or more chemicals, and an exposure to energy.

21. The system of claim 1, wherein the first holding material is positioned between the catheter and a first region of the prosthesis, and the second holding material is positioned between the catheter and a second region of the prosthesis.

22. The system of claim 21, wherein the first holding material is positioned between the catheter and an end of the prosthesis, and the second holding material is positioned between the catheter and a body of the prosthesis.

23. The system of claim 1, wherein the catheter defines a first lumen in fluid communication with a first port, and a second lumen in fluid communication with a second port.

24. The system of claim 23, wherein the first port is in fluid communication with the first holding material, and the second port is in fluid communication with the second holding material.

25. The system of claim 24, wherein the first lumen is configured to deliver the first stimulus to the first holding material, and the second lumen is configured to deliver the second stimulus to the second holding material.

* * * * *